United States Patent [19]
Flores et al.

[11] Patent Number: 5,817,699
[45] Date of Patent: Oct. 6, 1998

[54] PROCESS FOR THE PREPARATION OF KETAMINE OINTMENT

[76] Inventors: John A. Flores, POB 12182, San Bernardino, Calif. 92423; Kenton L. Crowley, 40970 Alton Ct., Temecula, Calif. 92591

[21] Appl. No.: 866,770

[22] Filed: May 30, 1997

[51] Int. Cl.⁶ .................................................. A61K 31/135
[52] U.S. Cl. .............................................................. 514/647
[58] Field of Search ............................................. 514/647

[56] References Cited

FOREIGN PATENT DOCUMENTS

4340767 C2   6/1995   Germany .

OTHER PUBLICATIONS

Budavari, Susan, Ed., The Merck Index, Eleventh Edition, entry No. 5174, p. 834. 1989.

Primary Examiner—Willam R.A. Jarvis
Attorney, Agent, or Firm—Rob L. Phillips

[57] ABSTRACT

The present invention relates to a process for producing a ketamine ointment that is self-administered topically by a subject to alleviate neuropathic, sympathetic medicated pain and myofacial pain said subject is experiencing. The present invention is also utilized to improve the motor skills, alertness, sleeping habits, energy level and overall well-being of a subject suffering from Parkinson's disease.

12 Claims, No Drawings

PROCESS FOR THE PREPARATION OF KETAMINE OINTMENT

FIELD OF THE INVENTION

The present invention relates to a process for producing a ketamine ointment. The present invention also relates to a method for treating sympathetic mediated pain, neuropathic pain, myofacial pain and Parkinson's disease with the resulting ketamine ointment.

BACKGROUND OF THE INVENTION

Ketamine is widely recognized as a general nonbarbiturate anesthetic that acts quickly to produce an anesthetic state. More specifically, ketamine is an acrylcycloalkylamine used traditionally in the induction of dissociative anesthesia. Ketamine has been used to induce anesthesia prior to elective surgery in healthy children. (Weksler, 1993, Can. J. Anaesthesia 40: p. 119–121) Ketamine has also been used to induce anesthesia in elderly patients who could not tolerate general anesthesia. Ketamine is usually administered intramuscularly or intravenously to induce anesthesia.

Ketamine has also been recognized as an analgesic. There have been clinical applications of ketamine for the treatment of various pain syndromes. Ketamine has been used successfully in the treatment of sympathetic mediated pain and various forms of neuropathic pain. Neuropathic pain is a pain that results from an abnormal functioning of the peripheral and/or central nervous system. Examples of neuropathic pain include, reflex dystrophy, trigeminal neuralgia and cutaneous nerve entrapment syndromes. Once again, ketamine was administered intramuscularly or intravenously to treat the various pain syndromes. In addition, ketamine was administered orally, subcutaneously and caudally in treating the aforementioned pain.

One major disadvantage of using ketamine has been the side-effects associated with its use. Ketamine's side-effects include sedation, hallucinations, dysphoria and amnesia. These side-effects manifest themselves with traditional methods of administering ketamine. The traditional methods of administering ketamine, including intramuscularly, intravenously, subcutaneously, orally or caudally, often times result in side-effects. Unfortunately, ketamine is only available commercially in a liquid injectable form, therefore the methods of administering ketamine are primarily limited to those mentioned. The side-effects associated with ketamine have restricted the use of ketamine to very controlled settings such as hospitals or clinics under the direct care of a physician with resuscitative equipment on standby.

Another disadvantage of administering ketamine with traditional methods is the difficulty in directing or concentrating the ketamine to the pain site. The traditional methods of administering ketamine lead to systemic effects of the medication and first pass degradation by the liver. In other words, the full effect of the ketamine is limited by the time a small percentage of the ketamine administered reaches the pain site.

Inability to direct ketamine to the pain site may also cause larger doses of ketamine to be used to insure that a larger percentage of the ketamine reaches the pain site. U.S. Pat. No. 5,543,434 describes a method for managing chronic pain by administering ketamine through the nasal passage. One advantage noted in U.S. Pat. No. 5,543,434 is that the invention avoids dosing a patient with large amounts of ketamine that may cause dysphoria or hallucinations. However, this method fails to direct or concentrate the ketamine to the pain site thereby possibly causing the patient to use the nasal inhaler repeatedly until the pain is alleviated. This continued use by the patient may cause excessive doses of ketamine in the patient. This repeated use may cause side-effects, similar to those associated with traditional applications of ketamine, and will definitely increase the cost of treatment.

SUMMARY OF THE INVENTION

Accordingly, the present invention relates to a process for producing a ketamine ointment, the composition of which, can be directly applied to a subject's pain site thereby rapidly alleviating the pain while avoiding ketamine's side-effects. The primary ingredients in the ointment are ketamine hydrochloride, lecithin organogel, ethoxy diglycol, pluronic F-127 gel, and deionized distilled water, where ethoxy diglycol is listed as Carbitol® in the Merck Index and lecithin organogel is the combination of the following ingredients in the concentrations similar to those indicated, Lecithin Soya Granular (10 gm), Isopropyl Palmitate NF (10 gm), and Sorbic Acid N-FCC Powder (0.2 gm) and Pluronic F-127 gel is a combination of the following ingredients in various concentrations depending on the percentage of Pluronic F-127 desired, Pluronic F-127 NF, Potassium Sorbate NF and Purified Water q.s. The novel process utilized to combine the ingredients maximizes the effectiveness of the ketamine ointment.

There are also initial findings that the ketamine ointment has useful applications in persons suffering from Parkinson's disease.

Other objects, features and advantages of the invention will be readily apparent from the following description of certain preferred embodiments. It is understood that modifications and variations may be effectuated without departing from the spirit and scope of the present invention.

DETAILED DESCRIPTION OF THE PREFERRED EMBODIMENTS

Producing the ketamine ointment is accomplished by combining ketamine hydrochloride, lecithin organogel, ethoxy diglycol, pluronic F-127 gel, and deionized distilled water through a series of novel steps. The process comprises the steps of:

(a) calculating the amount of ketamine hydrochloride, based on an overall volume desired, necessary to produce a ketamine ointment with a ketamine concentration level of between 10 mg/(cc of ointment)–100 mg/(cc of ointment);

(b) dissolving said amount of ketamine hydrochloride in 7% by volume ethoxy diglycol and 7% by volume hot deionized-distilled water;

(c) adding solution from step (b) to between 18% to 32% by volume lecithin organogel;

(d) adding to the solution from step (c) a sufficient amount by volume of pluronic F-127 gel, with a pluronic concentration level between 10%–40%, ensuring that said desired overall volume is achieved;

(e) mixing the solution from step (d) until the pluronic F-127 gel is added and the mixture is evenly distributed.

The resulting ketamine ointment has been used to treat neuropathic pain and sympathetic maintained pain including, but not limited to, carpal tunnel syndrome, abdominal cutaneous nerve entrapment syndrome, burns, occipital neuralgia, post herpetic neuralgia, trigeminal neuralgia, phantom limb pain and reflex sympathetic dystrophy of the extremities. The ketamine ointment has also been used to relieve myofacial pain. In nearly every situation the pain was relieved within 20–40 seconds. In many cases a pain level of 10 out of 10 intensity was reduced to a pain level of zero. In addition, the ketamine ointment has not produced any of the side-effects associated with the traditional methods of administering ketamine.

One advantage of the present invention is that it can be applied directly to the pain site on the subject to almost immediately alleviate the pain. Until now the use of topical ointments and creams as a route of medication or drug administration has been difficult to regulate reliably. The skin serves as a person's first line of defense against microbe invasion and chemicals. The skin is a matrix of proteins and lipids that are layered in such a way that many drugs, because of their complex structures, molecular weights and/or charges are not allowed to pass through the skin to the muscle or nerves underneath. Many chemicals have been developed to act as carriers to deliver the drug across the layers of skin. However, often times the carrier interacts with the drug to form an entirely new chemical structure that can potentially reduce the drugs potency or increase the drugs toxicity. The process followed to produce the present invention utilizes an emulsified carrier that allows the ketamine to pass through the skin without difficulty while not interacting with the ketamine to form a new chemical structure.

Another advantage of the present invention is that it avoids subjecting a patient to the side-effects associated with other routes of administration. The dosage levels remain relatively small since the ketamine is applied directly to the pain site.

An additional advantage of the present invention is that concentrated higher levels of medication can be applied at the pain site which would require 30 to 100 times the amount of medication by the other traditional methods of administering ketamine to produce the same analgesic effect. This can still be accomplished with no ketamine side-effects. In addition, the route of administration lowers the cost of treatment for the patient since no resuscitative equipment, doctors or other personnel need to be on standby.

An unexpected discovery related to the present invention is its effectiveness in treating Parkinson's disease. Application of the present invention to the neck and forearms of several Parkinson's patient dramatically improved the patient's motor skills and vision.

Yet another advantage of the present invention is the ease of application for the patient. There is no necessity for a doctor to administer the present invention. Once a person skilled in the art determines the dosage level of the present invention, administering the present invention is as simple as applying sun-tan lotion. Therefore, doctors do not have to be occupied giving patients shots of ketamine thereby alleviating the increasingly large backlog of patients at hospitals.

This ability to self-administer the present invention also lowers the total cost of treatment for the patient and the health care industry. Any improvement related to the health care industry is significant for society as a whole. It is no secret that the health care system is a major area of concern with its high costs. The present invention will eliminate many of the more costly and invasive treatments while long term disability is significantly reduced thereby alleviating part of the stress on the health care industry.

EXAMPLES (1)

The first case was for the treatment of an intercostal neuralgia. A 40 year old white female had developed a chronic pain on her left flank between the eighth and ninth ribs. The pain originally occurred after her primary physician removed a subcutaneous cyst at the same site. The pain originated at the site of the removed cyst but also referred to the left shoulder and neck. The pain was described as intermittent, sharp at times, and achy. The pain levels would escalate to levels of complete incapacitation and then subside to more tolerable levels, but never completely resolve.

The patient was tried on tricyclic antidepressants, neurontin, clonidine, nonsteroidals, and various combination opioid preparations without success. A nerve block was tried with limited success. The nerve block gave the patient relief for one week. A neurolytic procedure using phenol/glycerol at the site of the intercostal nerve gave the patient relief for a period of two months.

The patient was subsequently administered the ketamine ointment in the concentration of 10.0 mg/cc. Only 0.1 cc of ointment was applied to the site and within 30 seconds the patient had complete pain relief. The patient had complete pain relief at the site as well as complete resolution of the referred pain in the shoulder and neck. The duration of relief was one week per application. Each subsequent application of the ketamine ointment resulted in 100% relief of the patient's pain.

(2)

The second case was for the treatment of reflex sympathetic dystrophy. The patient was a women in her early 30's who had injured her left ankle in an accident. The pain was initially localized in the ankle, but within a period of a few months the pain began to spread throughout the entire limb. Within a year the patient was completely bedridden.

Prior to the application of the ketamine ointment, the patient was tried on various conventional medications used in the treatment of neuropathic pain. Physical therapy was tried, but unsuccessful.

The ketamine ointment was applied in the concentration range of 10–20 mg/cc. Trigger points along the limb or tender points were marked or mapped out. Each point was then treated by applying between 0.05 to 0.1 cc of the ointment. Pain relief was again quite rapid, but not complete. Continued application of the ointment on a daily basis reduced the number of trigger points from fifty to only one and significantly reduced a 10 out of 10 pain level to 2 out of 10 pain level in three months after all other treatments had failed over a six and a half year period.

(3)

The third study was for the treatment of phantom limb pain. A 24 year old male patient had his right hand amputated at the wrist. The ketamine ointment with a concentration level of 100 mg/cc was applied in 0.1 cc increments. The ketamine ointment was applied to the stump and also to the left hand secondary to a "mirror" effect.

The sympathetic phantom pain associated with the amputation was relieved in minutes. The patient's pain level decreased from 8 out of 10 to zero.

(4)

In addition to relieving pain, the ketamine ointment has been used in the treatment of some forms of Parkinson's disease. The patient was receiving the traditional medications, at maximum dosages, used to combat Parkinson's disease prior to the ketamine ointment. The Parkinson's patient was nonambulatory for two years prior to trying the ketamine ointment.

The ketamine ointment with a concentration of 20 mg/cc was applied to the patient's neck and forearms and approximately 20 minutes later the patient was able to raise unaided out of his wheelchair. In fact, the patient literally ran down the hallway of the medical center where he was receiving his traditional treatment.

Benefit continued over the following two months until the present. Besides dealing with gait freezing associated with Parkinson's disease, the ketamine ointment has improved the patient's alertness, sleeping, energy level and overall sense of well-being.

What is claimed is:

1. A process for the preparation of ketamine ointment comprising the steps of
    a) calculating the amount of ketamine hydrochloride, based on an overall volume desired, necessary to produce a ketamine ointment with a ketamine concentration level of between 10 mg/cc–100 mg/cc;
    (b) dissolving said amount of ketamine hydrochloride in 7% by volume ethoxy diglycol and 7% by volume hot deionized-distilled water:
    (c) adding solution from step (b) to between 18% to 32% by volume lecithin organogel;
    (d) adding to the solution from step (c) a sufficient amount by volume of pluronic F-127 gel, with a pluronic concentration level between 10%–40%, ensuring that said desired overall volume is achieved;
    (e) mixing the solution from step (d) until the pluronic F-127 gel is added and an evenly distributed mixture is achieved.

2. Ketamine ointment produced in accordance with the process of claim 1.

3. A process according to claim 1 wherein said steps (b) through (e) are accomplished by using two syringes and a luer-lock adapter to push said ingredients back and forth between said syringes until said evenly distributed mixture is achieved.

4. Ketamine ointment produced in accordance with the process of claim 3.

5. A process according to claim 1 wherein said ingredients are combined by ultrasonic means until said evenly distributed mixture is achieved.

6. Ketamine ointment produced in accordance with the process of claim 5.

7. A method for treating pain in a subject comprising self-administering topically said ketamine ointment produced in accordance with the process of claim 1.

8. The method according to claim 7, comprising administering a sufficient amount of said ketamine ointment to insure a proper dose of ketamine to alleviate neuropathic pain.

9. The method according to claim 7, comprising administering a sufficient amount of said ketamine ointment to insure a proper dose of ketamine to alleviate sympathetic maintained pain.

10. The method according to claim 7, comprising administering a sufficient amount of said ketamine ointment to insure a proper dose of ketamine to alleviate myofacial pain.

11. A method for treating Parkinson's disease in a subject comprising administering topically said ketamine ointment produced in accordance with the process of claim 1 containing a concentration of ketamine between 10 mg/cc–100 mg/cc which is sufficient to improve the motor skills, alertness, sleeping habits, and energy level of said subject suffering from Parkinson's disease but beneath a level to cause side-effects associated with ketamine.

12. The method according to claim 11, whereby said ketamine ointment is topically applied to neck and forearms of said subject afflicted with Parkinson's disease.

* * * * *